United States Patent [19]

Hunt et al.

[11] Patent Number: 5,077,104
[45] Date of Patent: Dec. 31, 1991

[54] NICOTINE PACKAGING MATERIALS

[75] Inventors: James A. Hunt, Fremont; James L. Osborne, Mountain View; John T. Dunn, Redwood City; Melinda K. Nelson, Sunnyvale; Nathan Roth, San Francisco, all of Calif.

[73] Assignee: Alza Corporation

[21] Appl. No.: 454,257

[22] Filed: Dec. 21, 1989

[51] Int. Cl.$^5$ .............................................. B65D 30/08
[52] U.S. Cl. .................... 428/34.3; 206/229; 206/440; 206/441; 206/484; 424/448; 424/449; 428/35.2; 428/35.3; 428/35.4; 428/216; 428/424.8; 428/462
[58] Field of Search ..................... 428/34.3, 35.2, 35.3, 428/35.4, 462, 424.8, 216; 424/449, 448; 206/484, 440, 229, 441

[56] References Cited

U.S. PATENT DOCUMENTS

| | | |
|---|---|---|
| 3,252,802 | 5/1966 | Cunningham . |
| 3,426,102 | 2/1969 | Solak et al. . |
| 3,845,217 | 10/1974 | Ferno et al. . |
| 3,870,794 | 3/1975 | Hutchinson et al. ............... 424/264 |
| 3,877,468 | 4/1975 | Lichtneckert et al. ................ 131/2 |
| 4,139,665 | 2/1979 | Herrero ............................ 428/36.7 |
| 4,265,948 | 5/1981 | Hayes ................................. 428/462 |
| 4,387,126 | 6/1983 | Rebholz ............................ 428/35.3 |
| 4,597,961 | 7/1986 | Etscorn ............................... 424/28 |
| 4,665,069 | 5/1987 | Rosenberg ......................... 514/222 |
| 4,680,172 | 7/1987 | Leeson ............................... 424/449 |
| 4,715,387 | 12/1987 | Rose .................................... 131/270 |
| 4,748,181 | 5/1988 | Hutchinson et al. ............... 514/343 |
| 4,758,434 | 7/1988 | Kydonieus et al. . |
| 5,008,110 | 4/1991 | Benecke ............................. 424/448 |

FOREIGN PATENT DOCUMENTS

| | | |
|---|---|---|
| 8145487 | 5/1988 | Australia . |
| 0251425 | 1/1988 | European Pat. Off. . |
| 3438284 | 3/1985 | Fed. Rep. of Germany . |
| 2171906A | 9/1986 | United Kingdom . |

OTHER PUBLICATIONS

Robert H. Linnell, *The Oxidation of Nicotine. I. Kinetics of the Liquid Phase Reaction Near Room Temperature*, Tobacco, vol. 150, No. 18, pp. 187–190, Apr. 29, 1960.

F. Paul Gavin and Robert H. Linnell, *Autoxidation of Nicotine. II. Products and Proposed Mechanism*, Tobacco, pp. 32–35.

S. H. Gehlbach, M.D., et al., *Protective Clothing as a Means of Reducing Nicotine Absorption in Tobacco Harvesters*, Archives of Environmental Health, Dept. of Human Resources, Division of Health Services, Raleigh, N.C., Mar./Apr. 1979.

H. Schievelbein, *Nicotine, Resorption and Fate*, Pharmac, Ther. vol. 18, pp. 233–248, (Great Britain) copyright Pergamon Press, Ltd., 1982.

(List continued on next page.)

*Primary Examiner*—Ellis P. Robinson
*Assistant Examiner*—Rena L. Dye
*Attorney, Agent, or Firm*—Steven F. Stone; Edward L. Mandell; Paul L. Sabatine

[57] ABSTRACT

The invention herein pertains to methods and materials for producing a nicotine maintenance pouch. Laminates comprising a nicotine barrier layer and a nicotine degradation agent barrier layer are disclosed. In a preferred embodiment, the nicotine barrier layer comprises a nitrile rubber modified acrylonitrile-methyl acrylate copolymer. An especially preferred nicotine barrier material comprises, by weight percent, 75% acrylonitrile, and 25% methyl acrylate with 10% butadiene (AN-MA/B). The nicotine degradation agent barrier layer is preferably aluminum foil. In an especially preferred embodiment, the laminate comprises a layer of AN-MA/B adhered to a layer of aluminum foil, which in turn is adhered to a layer of paper stock.

Pouches comprising a self-sealed nicotine barrier layer and a nicotine degradation agent barrier layer are disclosed. These pouches are preferably formed from the laminates above.

A method for production of pouches comprising: (a) providing a laminate including a self-sealable nicotine barrier layer and a nicotine degradation agent barrier layer; and (b) sealing the self-sealable nicotine barrier layer to enclose a nicotine device.

7 Claims, 3 Drawing Sheets

OTHER PUBLICATIONS

C. Carruthers and A. Neilson, *A Simplified Procedure for the Gas Chromatographic Determination of Nicotine: Application of the Method to Mouse Skin*, Mikrochimica Acta (Wien), pp. 59–66, copyright Springer-Verlage, 1980.

Rose et al., *Transdermal Administration of Nicotine*, Drug and Alcohol Dependence, 13 (1984), pp. 209–213, Elsevier Scientific Publishers Ireland Ltd.

Rose et al., *Transdermal Nicotine Reduces Cigarette Craving and Nicotine Preference*, Clin. Pharmacol Ther., vol. 38, No. 4, pp. 450–456 (1985).

Business Abstracts 12, *Chemical Marketing Reporter*, pp. 5, 15 (1987).

6th World Conference on Smoking and Health, Abtracts Nov. 9–12, 1987, Japan.

Michael A. H. Russell, *Nicotine Replacement: The Role of Blood Nicotine Levels Their Rate of Change, and Nicotine Tolerance, Nicotine Replacement: A Critical Evaluation*, pp. 63–94.

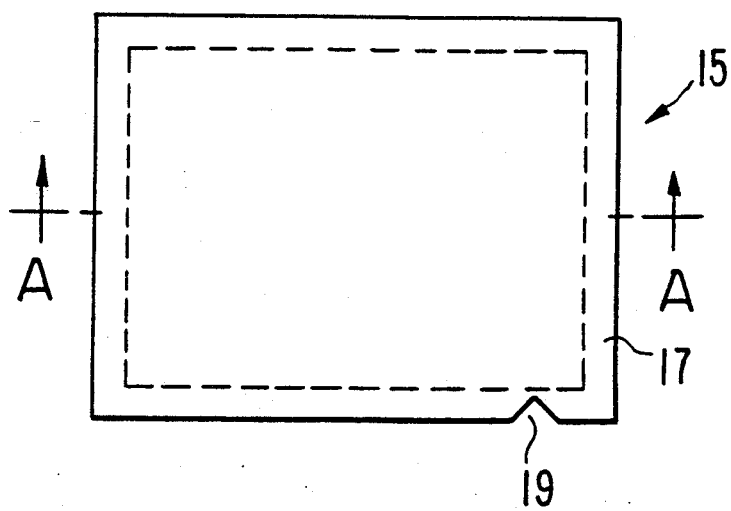
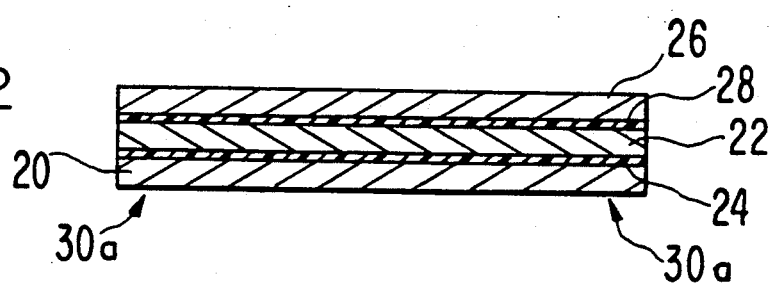
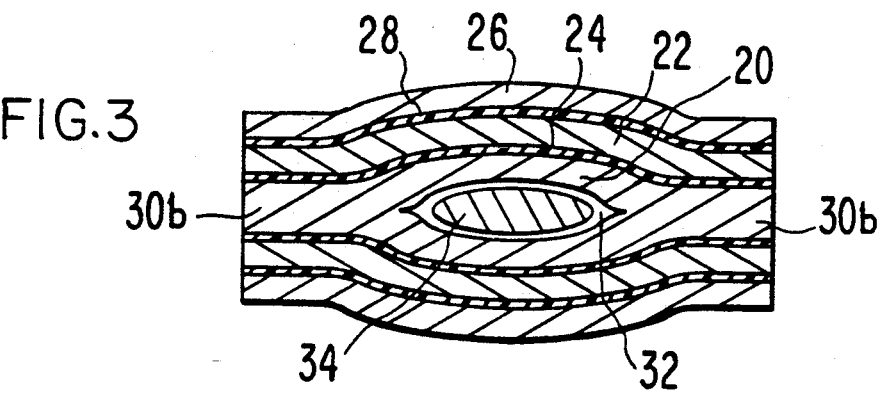
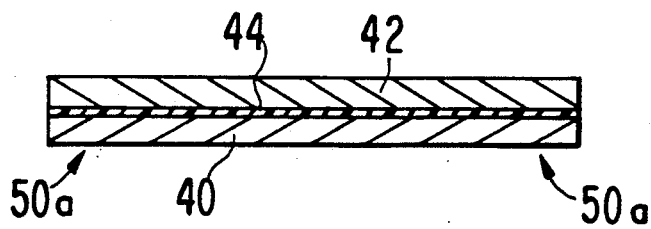
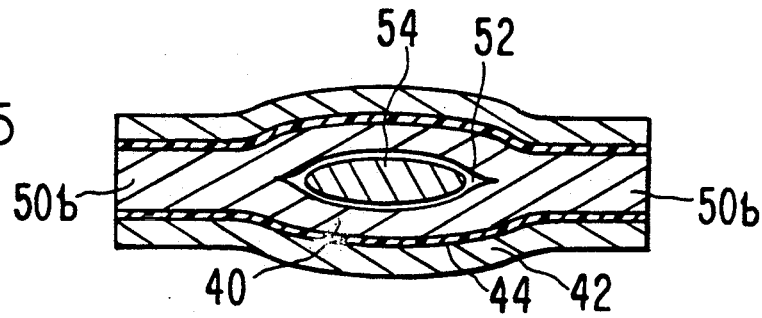

NICOTINE PACKAGING MATERIALS

TECHNICAL FIELD

The invention herein pertains to materials and methods for the manufacture of nicotine storage pouches.

BACKGROUND ART

Nicotine base is a reactive species which decomposes in the presence of oxygen or light. It is highly hygroscopic. Nicotine base causes the solvation of standard adhesives, which cannot be effectively used to seal nicotine-containing pouches.

The problem of providing containment for consumer products containing nicotine base has heretofore found no simple solution. A transdermal system for the delivery of nicotine is disclosed in Australian Patent Application Au-A-81454/87. In that system two nicotine precursors are sealed in burstable pouches. Only after application to skin and rupture of the pouches is the highly reactive nicotine base formed.

It is very desirable to provide a container which can hold one or more nicotine-containing devices. Such a container must be inert to nicotine; that is, it must not cause degradation of nicotine base, or be degraded by nicotine. The container must act as a barrier to nicotine. A nicotine barrier permits less than 1% nicotine migration over a period of six months, more preferably less than 0.5% migration, and most preferably is impermeable to nicotine. Because nicotine acts as a solvent to standard adhesives, the barrier material must be sealable to itself, such as by heatsealing. The seal must provide a stable bond which does not provide a path for nicotine migration out of the package.

The container must also act to exclude agents which are detrimental to the stability of nicotine base. Air (oxygen) and light both act to decompose nicotine base. In addition, nicotine is strongly hygroscopic, and water in liquid or vapor form will be adsorbed into the nicotine base, causing a change in nicotine concentration.

Materials which provide a barrier to nicotine and provide protection from nicotine degradation agents include metal foils such as aluminum foil, polyesters such as polyethylene terephthalate (PET), and poly(tetrafluorethylene) (PTFE). These materials are not self-sealable, and adhesive or heat sealable coatings on the surface of these materials can provide a path for migration of nicotine out of the package. Traditional self-sealable pouching materials such as polyvinyl fluoride (PVF), polyvinylidene fluoride (PVDF), chlorotrifluoroethylene (CTFE), low density polyethylene (LDPE), and high density polyethylene (HDPE) do not provide an effective nicotine barrier.

We have unexpectedly discovered that nitrile rubber modified acrylonitrile-methyl acrylate copolymers of the type, commercially available as BAREX TM, can be used as a heat sealable material in pouches to provide an effective barrier to nicotine migration even over extended periods of time.

It is therefore an object of this invention to provide a container for nicotine base or for products containing nicotine base.

It is an object of this invention to provide a self-sealable, pouchable material which acts as a barrier to nicotine.

It is another object of the invention to provide a pouching material which acts as a barrier to nicotine degradation agents such as air (oxygen), water in liquid or vapor form, and light.

It is yet another object of the invention to provide a pouch which is suitable for long-term containment of nicotine-containing transdermal delivery devices.

BRIEF DESCRIPTION OF DRAWINGS

FIG. 1 shows a top view of a pouch of this invention.

FIG. 2 shows a cross-sectional representation of a laminate useful to form a pouch of FIGS. 1.

FIG. 3 shows a cross section of the pouch of FIG. 1 taken through line A—A. The pouch has been formed of the laminate of FIG. 2.

FIGS. 4, 6, 8 and 10 show representations of the laminates used to form the pouches of FIGS. 5, 7, 9 and 11, respectively.

FIGS. 7 through 11 show views of alternate embodiments of a pouch such as that shown in FIG. 1.

BRIEF DESCRIPTION OF INVENTION

Figure 6:
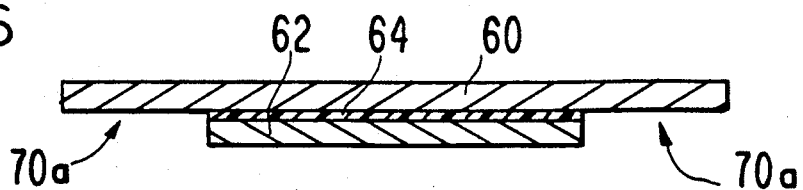

The invention herein pertains to methods and materials for producing a nicotine maintenance pouch.

Laminates comprising a nicotine barrier layer and a nicotine degradation agent barrier layer are disclosed. In one embodiment, the nicotine barrier layer comprises nitrile rubber modified acrylonitrile-methyl acrylate copolymer. An especially preferred nicotine barrier material comprises, by weight percentage, 75% acrylonitrile, and 25% methyl acrylate with 10% butadiene (AN-MA/B). A preferred nicotine degradation agent barrier layer is aluminum foil. In an especially preferred embodiment, the laminate comprises a layer of AN-MA/B adhered to a layer of aluminum foil, which in turn is adhered to a layer of paper stock.

Pouches comprising a self-sealed nicotine barrier layer and a nicotine degradation agent barrier layer are disclosed. These pouches are preferably formed from the laminates above.

A method for production of pouches comprises: (a) providing a laminate including a self-sealable nicotine barrier layer and a nicotine degradation agent barrier layer; and (b) sealing the selfsealable nicotine barrier layer to enclose a nicotine device.

DISCLOSURE OF INVENTION

Nicotine (beta-pyridyl-alpha-N-methylpyrrolidine) is a colorless liquid alkaloid derived from tobacco or by synthetic manufacture. It is a strongly alkaline, hygroscopic liquid which decomposes upon exposure to air (oxygen) or light.

As used herein, the term "pouch" refers to a package or other container which is generally flexible and is sealed on at least one side. The sealed pouches of this invention can comprise, for example, two sheets or lamina which have been joined along all edges; a single sheet or lamina which has been folded and sealed along all edges or along all non-fold edges; a bag or pocket which is sealed along one or more edges; and the like.

"Self-sealing" refers to the ability of a material to form a stable bond between one face of the material and another face of the same material. Self-sealing is accomplished, for example, by heat (thermal bar) sealing, impulse, radio frequency, ultrasonic sealing, and the like.

The term "nicotine barrier", as used herein, refers to a self-sealable film material which acts as a barrier to nicotine base: the barrier material does not permit migration of nicotine base through the material over time. The nicotine barrier material is also inert to nicotine: nicotine does not act as a solvent for the barrier material, and it does not plasticize the material, stress crack or craze the barrier material, or otherwise affect the physical characteristics of the material.

As used herein, "nicotine degradation agents" refer to oxygen, water in liquid or vapor form, and light. A "nicotine degradation agent barrier" is a barrier layer which is substantially impermeable to one or more nicotine degradation agent. "Nicotine maintenance" refers to the long-term storage of nicotine base, especially as embodied in a nicotine device, without migration of the nicotine out of the storage container, and without substantial degradation of the nicotine by oxygen, water, or light.

The term "nicotine device", as used herein, refers to an object which contains nicotine such as nicotine base, and especially a transdermal delivery device which includes nicotine base.

The preferred pouching material is a self-sealable laminate comprising a nicotine barrier and a nicotine degradation agent barrier. The nicotine maintenance combination of nicotine barrier and nicotine degradation agent barrier provides for simultaneous containment of the nicotine and protection of the nicotine from degradation.

The preferred nicotine barrier material is a nitrile rubber modified acrylonitrile-methyl acrylate copolymer. Preferably the nicotine barrier material comprises (by weight percent) a graft copolymer of about 73 to 77% acrylonitrile, and from about 23 to 27% methyl acrylate in the presence of about 8 to 10 parts by weight of butadiene-acrylonitrile copolymers containing approximately 70 percent by weight of polymer units derived from butadiene. An especially preferred nicotine barrier material comprises, by weight percent, about 75% acrylonitrile, and about 25% methyl acrylate with about 10% butadiene-acrylonitrile copolymer (AN-MA/B). This material disclosed, for example, in U.S. Pat. No. 3,426,102, and is commercially available as BAREX TM 210 resin from BP Chemicals International, Cleveland, OH. BAREX TM is also available as a film from Greenway Industries Corp., West Paterson, N.J.

Various compositions of the nicotine barrier AN-MA/B are available, for example, BAREX TM 210, 214 and 218. For simplicity of discussion, a film of AN-MA/B which is self-sealed by heat sealing, the currently preferred embodiment, is presented. This is for purposes of exemplification only and not by way of limitation.

AN-MA/B film thickness will generally be from about 0.8 mil or less to about 2.5 mil or greater, and is preferably from about 1.5 mil to about 2.0 mil. Thinner films can be used as long as the finished pouch is well-sealed and provides the requisite impermeability to the nicotine. Thicker films can be used as long as the sealing properties are not adversely affected, i.e., as long as the thicker films are sealed properly with the heat-sealing equipment used. Films should not be so thick that the seal provides a path for oxygen and water migration into the pouch.

While AN-MA/B is an excellent nicotine barrier, alone it provides insufficient protection from nicotine degradation agents to yield a good long-term storage container for nicotine or nicotine products.

The transmission of oxygen by BAREX TM 210 is reported as 0.8 $cm^3$ mil/100 $in^2$ 24 hr., atm. The water vapor transmission rate of BAREX TM 210 is 5.0 g mil/100 $in^2$ day at 100° F. and 100% relative humidity. BAREX TM 210 was tested at 30° C., and at 10% and 90% relative humidity to determine the water uptake. After four hours the film at 10% RH had absorbed 0.32 wt.% water. After four hours the film at 0.90% RH had absorbed 2.4 wt.% water. This amount of water absorption is sufficient to permit water uptake by nicotine base, causing dilution of the nicotine over time.

While such oxygen and water transmission rates are sufficient for most industrial purposes, they are sufficiently high to permit the decomposition of nicotine over time.

AN-MA/B is available in untinted (light straw) and blue-tinted transparent forms. These provide insufficient light protection to avoid nicotine decomposition by light.

To provide nicotine maintenance the AN-MA/B nicotine barrier must be augmented with a nicotine degradation agent barrier, which acts to inhibit the transmission of oxygen (air), water in the liquid and vapor forms, and light. The nicotine degradation agent barrier is generally a sheet of aluminum or other metal foil. Aluminum foil is preferred for cost and availability. The thickness of the aluminum foil is generally from less than 0.35 mil to 1 mil or greater. Foils less than 0.35 mil can be used when the foil is of sufficient quality that irregularities and holes are minimized. Foils thicker than 1 mil can be used, but tend to make the lamination process more difficult and the finished package somewhat stiffer.

In a preferred embodiment, the nicotine barrier and nicotine degradation agent barrier are adhered to form a laminate. The laminate can be formed using a urethane adhesive such as Adcote TM 548 (Morton Chemical Co., Woodstock, IL). In a currently less preferred embodiment, the AN-MA/B film can be metalized.

It may be desirable to provide an additional laminate layer which comprises a paper sheet. The paper provides the finished pouch with an attractive protective covering, and is a good substrate for printing. Paper weight is not critical as long as it does not interfere with the sealing process, and 35# kraft paper or 35# clay coat paper are adequate. The paper layer, if present, can be adhered with an adhesive such as polyethylene.

The nicotine maintenance pouches can be in any convenient form that permits the effective closure of the pouching materials and the formation of a substantially complete nicotine barrier. The perimeter of the pouches can be, for example, oval, circular, triangular, irregularly shaped, square, rectangular, and the like. For ease of manufacturing when the pouch is heat sealed, a square or rectangular shape is preferred.

The nicotine maintenance laminate can be self-sealed to form a pouch using any appropriate methods such as heat (thermal bar) sealing, impulse sealing, radio frequency sealing, ultrasonic sealing, and the like.

Referring now to the drawings, FIG. 1 is a top view of a pouch 15 according to this invention. The edges 17 are sealed to form an enclosure which is substantially impermeable to nicotine and to nicotine degradation agents. A simple cut, or a notch 19 can be placed in the sealed edge area 17 to assist in opening the pouch.

FIG. 2 is a cross-sectional view of a self-sealable laminate which is useful for producing pouches of this invention. The selfsealable AN-MA/B nicotine barrier layer 20 is adhered to the aluminum foil nicotine degradation agent barrier layer 22 by an ADCOTE ™ 548 adhesive layer 24. A 35# kraft paper coating layer 26 is adhered to the nicotine degradation agent barrier layer 22 by a 7# polyethylene adhesive layer 28. The laminate can be self-sealed, for example, at edges 30a.

FIG. 3 is a cross-sectional representation of the preferred embodiment of the pouch 14 of FIG. 1, taken across line A—A. It is formed from the laminate of FIG. 2. The self-sealing nicotine barrier layer 20 has been sealed at the edges 30b and forms an enclosure 32. Within the enclosure 32 is a nicotine device 34 such as a transdermal delivery device for the transport of nicotine base across the skin barrier.

FIG. 4 is a cross-sectional view of a an alternate self-sealable laminate which is useful for producing pouches of this invention. The self-sealable nicotine barrier layer 40 is adhered to the nicotine degradation agent barrier layer 42 by an adhesive layer 44. The laminate has self-sealable edges 50a.

FIG. 5 is an alternate cross-sectional representation of the pouch 14 of FIG. 1, taken across line A—A. It is formed from the laminate of FIG. 4. The self-sealing nicotine barrier layer 40 has been sealed at the edges 50b and forms an enclosure 52. Within the enclosure 52 is a nicotine device 54.

FIG. 6 is a cross-sectional view of a an alternate self-sealable laminate. The self-sealable AN-MA/B nicotine barrier layer 60 is adhered to the aluminum foil nicotine degradation agent barrier layer 62 by an adhesive layer 64. The nicotine degradation agent barrier layer 62 and adhesive layer 64 do not completely cover the nicotine barrier layer 60. Edges 70a are uncoated, and are available for self-sealing.

Figure 7:
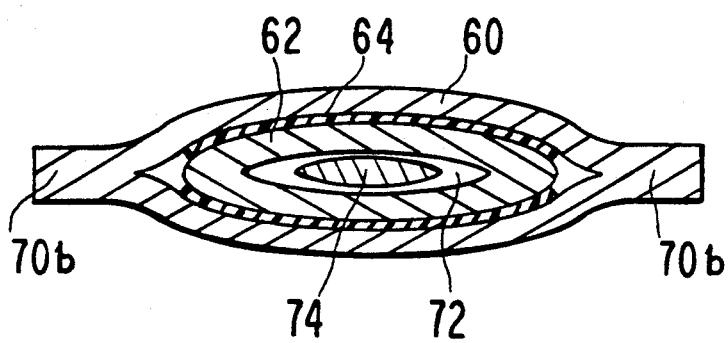

FIG. 7 is a cross-sectional representation of the pouch 15 of FIG. 1, taken across line A—A, formed from the laminate of FIG. 6. The self-sealing nicotine barrier layer 60 has been sealed at the edges 70b. The nicotine degradation agent barrier 62 and adhesive layer 64 are interior to the nicotine barrier layer 60, and, together with the nicotine barrier layer 60, form an enclosure 72. Within the enclosure 72 is a nicotine device 74.

Figure 8:
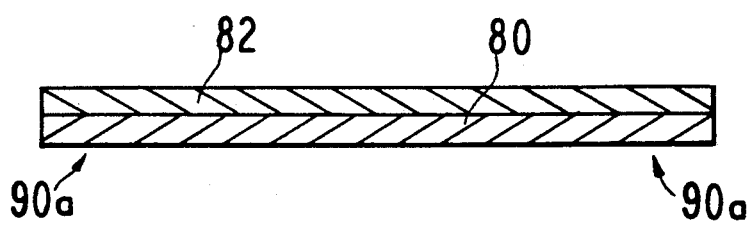

FIG. 8 is a cross-sectional view of a an alternate self-sealable laminate. The self-sealable nicotine barrier layer 80 has been metalized, and a layer of aluminum provides the nicotine degradation agent barrier layer 82. The laminate has self-sealable edges 90a.

Figure 9:
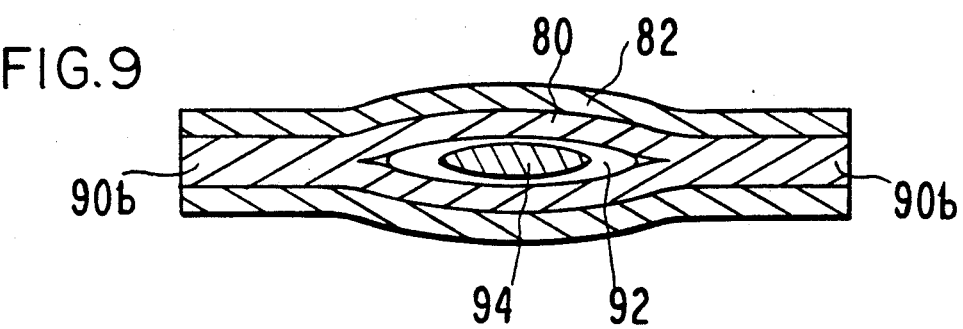

FIG. 9 is a cross-sectional representation of the pouch 15 of FIG. 1, taken across line A—A which has been formed from the laminate of FIG. 8. The self-sealing nicotine barrier layer 80 has been sealed at the edges 90b and forms an enclosure 92. Within the enclosure 92 is a nicotine device 94.

Figure 10:
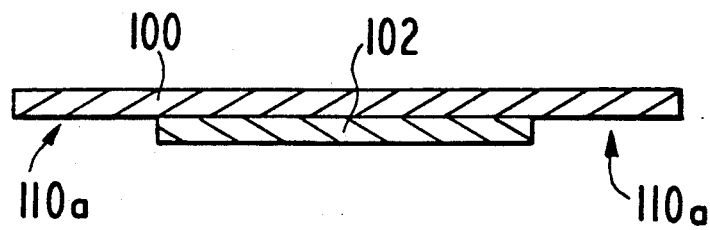

FIG. 10 is a cross-sectional view of a self-sealable laminate. The self-sealable nicotine barrier layer 100 has been selectively metalized with aluminum to produce a nicotine degradation agent barrier layer 102 which does not obstruct the edges 110a of the nicotine barrier layer 100.

Figure 11:
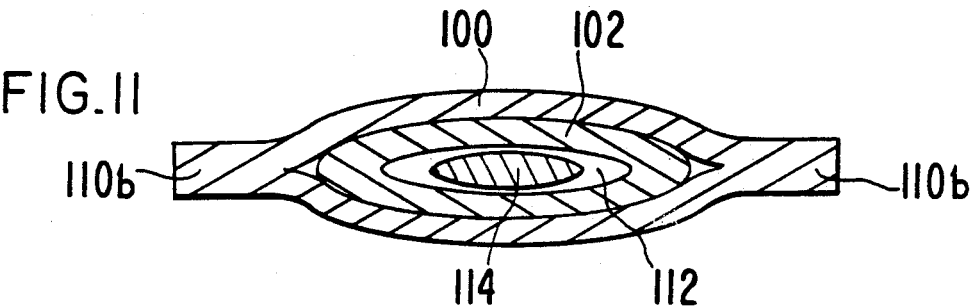

FIG. 11 is a cross-sectional representation of the pouch 15 of FIG. 1, taken across line A—A, formed from the laminate of FIG. 10. The self-sealing nicotine barrier layer 100 has been sealed at the edges 110b. The nicotine degradation agent barrier 102 is interior to the nicotine barrier layer 100, and, together with the nicotine barrier layer 100, forms an enclosure 112. Within the enclosure 112 is a nicotine device 114.

The following examples are illustrative of the present invention. They are not to be construed as limitations of the scope of the invention. Variations and equivalents of these examples will be readily apparent to one skilled in the art in light of the present disclosure, and the Claims herein. All percentages are weight percentages, and all temperatures are in degrees Celsius, unless otherwise noted.

EXAMPLE 1

Figure 12:
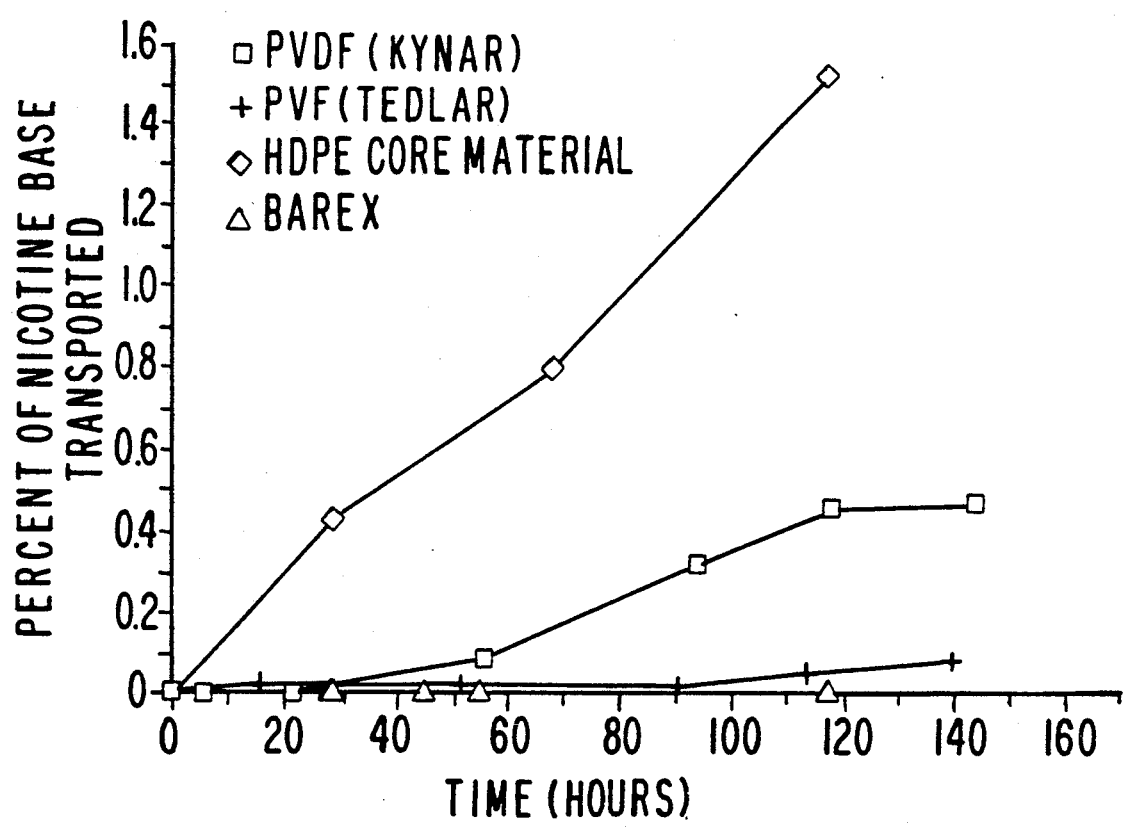
FIG. 12 shows comparative nicotine transmission data for various barrier materials.

Comparison of Nicotine Barrier Pouches 5.0 mL nicotine base was heat-sealed within a pouch made of a 2 mil BAREX ™ film. The outside dimensions of the pouch were approximately 3 cm by 6 cm. The pouch was placed in a bottle with 50 g. distilled water. The bottle was maintained at 51° C. in a water bath. Nicotine migration through the pouch was determined, and is shown in FIG. 12.

The above procedure was repeated, substituting for the BAREX ™ film a 2 mil film of (polyvinyl fluoride (PVF), duPont de Nemours, Wilmington, Del.). Nicotine migration through the pouch was determined, and is shown in FIG. 12. The migration of nicotine through TEDLAR ® was minimal for about 90 hours but began to increase toward significant levels thereafter.

The above procedure was repeated, substituting for the BAREX ™ film a 3 mil film of KYN (polyvinylidene fluoride (PVDF), Westlake Plastics Co., Lenni, PA). Nicotine migration through the pouch was determined, and is shown in FIG. 12.

(The above procedure was again repeated, substituting for the BAREX ™ film pouch a diffusion cell of ACLAR ™ (chlorotrifluoroethylene (CTFE), Allied Chemical Corp., Morristown, N.J.). 1.5 mil and 3 mil cells of the copolymer ACLAR ™ 22A, and 1 mil cell of the tripolymer ACLAR ™ 33C were tested. The cells suffered failure due to stress cracks.

The above procedure was again repeated, substituting for the BAREX ™ film a 2 mil film of HDPE (high density polyethylene core material, stripped pouch stock, Richmond Technology, Redlands, CA) laminated with 1 mil aluminum foil and 35# Kraft paper (lamina provided by Richmond Technology). Nicotine migration through the pouch was determined, and is shown in FIG. 12.

EXAMPLE 2

Nicotine Barrier Pouches

A 1.5 mil thickness of BAREX ™ 210 (Greenway Industries Corp.) was laminated with 1 mil aluminum foil using Adcote 548 adhesive with Catalyst F (Morton Chemical Co., Woodstock, IL). The aluminum foil was then bonded to a 35# Kraft paper using 7# polyethylene, to produce a laminate. The laminate was passed through a Circle Design (2-up) packager (Paxall Circle Design Machinery) having, at each sealing station, a metal heat bar at 425° F. and an opposed rubber heat bar at 300° F. Sufficient pressure was applied to provide a good seal. A transdermal nicotine delivery device according to copending patent application Ser. No. 06/906,730 now U.S. Pat. No. 4,908,027 was enclosed within the pouch. The nicotine device demonstrated good stability over time.

A 1.5 mil thickness of BAREX ™ 210 (Greenway Industries Corp.) was laminated with 0.35 mil aluminum foil using Adcote 548 adhesive with Catalyst F (Morton Chemical Co., Woodstock, IL). The aluminum foil was then bonded to a 35# clay coat paper using 7# polyethylene, to produce a laminate. The laminate was formed into a nicotine device containing pouch as above. The nicotine device demonstrated good stability over time.

A 2.5 mil thickness of BAREX ™ 210 (Greenway Industries Corp.) was laminated with 0.35 mil aluminum foil using Adcote 548 adhesive with Catalyst F (Morton Chemical Co., Woodstock, IL). The aluminum foil was then bonded to a 35# clay coat paper using 7# polyethylene, to produce a laminate. The laminate was formed into a nicotine device containing pouch as above. The nicotine device demonstrated good stability over time.

While the present invention has been described in terms of laminated pouched storage devices, it will be apparent to one skilled in the art that variations, modifications and substitutions can be made. These variations, modifications and substitutions can be made without departing from the scope of our invention, which is limited only by the following claims.

We claim:

1. A nicotine maintenance pouch enclosing a nicotine containing device, the walls of the pouch comprising:
   (a) a self-sealed nicotine barrier member completely enclosing said nicotine device and consisting essentially of a nitrile rubber modified acrylonitrile/methyl acrylate copolymer;
   (b) a first adhesive layer disposed on a surface of said nicotine barrier member;
   (c) a nicotine degradation agent barrier bonded to said nicotine barrier member by said first adhesive;
   (d) a second adhesive upon the external surface of the laminate formed by elements (a), (b) and (c); and
   (e) an external protective layer bonded to said laminate by said second adhesive layer.

2. The pouch of claim 1 wherein said copolymer comprises a graft copolymer formed from about 73-77% acrylonitrile and from about 23-27% methyl acrylate copolymerized in the presence of about 8-10 parts by weight of butadiene/acrlonitrile copolymers containing approximately 70% by weight of polymer units derived from butadiene, said nicotine degradation agent barrier is aluminum foil and said protective layer is paper.

3. The pouch of claim 1 wherein said nicotine barrier member forms the inner surface of said pouch.

4. A pouch according to claim 2 wherein the nicotine barrier member is from about 0.8 mil to about 2.5 mil thick.

5. A pouch according to claim 4 wherein said nicotine barrier member copolymer consists of about 75% acrylonitrile and about 25% methyl acrylate with about 10 parts by weight butadiene/acrylonitrile copolymer.

6. A pouch according to claim 4 wherein the nicotine degradation agent barrier layer comprises aluminum foil having a thickness of from about 0.35 mil to about 1 mil.

7. A pouch according to claim 4 wherein said nicotine device further comprises a device for the transdermal delivery of nicotine base.

* * * * *